(12) United States Patent
Felsberg

(10) Patent No.: US 8,538,101 B2
(45) Date of Patent: Sep. 17, 2013

(54) IMAGE RECONSTRUCTION

(76) Inventor: Michael Felsberg, Linköping (SE)

( * ) Notice: Subject to any disclaimer, the term of this patent is extended or adjusted under 35 U.S.C. 154(b) by 508 days.

(21) Appl. No.: 12/599,673

(22) PCT Filed: Aug. 10, 2007

(86) PCT No.: PCT/SE2007/000721
§ 371 (c)(1),
(2), (4) Date: Feb. 1, 2011

(87) PCT Pub. No.: WO2009/022946
PCT Pub. Date: Feb. 19, 2009

(65) Prior Publication Data
US 2011/0142311 A1 Jun. 16, 2011

(51) Int. Cl.
*G06K 9/00* (2006.01)
(52) U.S. Cl.
USPC ........... 382/128; 382/129; 382/130; 382/131; 378/4
(58) Field of Classification Search
USPC ...................... 382/128–131; 378/4
See application file for complete search history.

(56) References Cited

U.S. PATENT DOCUMENTS

| 6,317,478 | B1 * | 11/2001 | Patch | 378/4 |
| 7,206,440 | B2 * | 4/2007 | August | 382/131 |
| 7,251,307 | B2 * | 7/2007 | Chen | 378/4 |
| 2006/0109952 | A1 | 5/2006 | Chen | |

FOREIGN PATENT DOCUMENTS

| WO | WO 2007/010206 A1 | 1/2001 |
| WO | WO 2005/121836 A1 | 12/2005 |
| WO | WO 2005121836 A1 * | 12/2005 |

OTHER PUBLICATIONS

The monogenic signal, Felsberg et al.,IEEE, 1053-587X, 2001, pp. 3136-3144.*
The monogenic scale—space., Felsberg et al., Document D7, 2004, pp. 5-26.*
The monogenic Scale space on a rectangular—Features., Felsberg et al., Springer, Document D2, 2005, pp. 187-201.*
The Monogenic Scale Space on a Rectangular Domain and its Features, pp. 187-201,—2005.
Uniform Estimation of Orientation Using Local and Nonlocal 2-D Energy Operators,—2005.
The Monogenic Scale—Space: A Unifying Approach to Phase-Based Image Processing in Scale-Space, pp. 5-26,—2004.
The Monogenic Signal, pp. 3136-3144,—2001.

* cited by examiner

*Primary Examiner* — Jayesh A Patel
(74) *Attorney, Agent, or Firm* — Birch, Stewart, Kolasch & Birch, LLP

(57) ABSTRACT

An apparatus for reconstructing an image from the derivative of a sinogram includes means (26) for multiplying a projection orientation unit vector field (24) with the derivative to form an oriented derivative, means (28) for back-projecting the oriented derivative, and means (30-40) for Riesz transforming the back-projected oriented derivative.

15 Claims, 10 Drawing Sheets

(a) RAMP FILTER (b) HILBERT TRANSFORM (c) RIESZ TRANSFORM (d) CURL (ERROR)

(a) (b)

(a) (b)

IMAGE RECONSTRUCTION

TECHNICAL FIELD

The present invention relates to image reconstruction from line projections.

BACKGROUND

In many applications it is desirable to reconstruct an image from a number of line projections of the image forming a so called sinogram. This type of problem occurs in many different contexts, e.g., in computer tomography (CT) slice reconstruction (both in medical and non-medical applications, such as material inspection and safety control), helical cone beam reconstruction (image reconstruction in the Katsevich plane), and Hough transform techniques in image analysis.

Although a number of methods for such reconstruction are known, see for example [1-3], in practical implementations these methods suffer from either aliasing or noise problems, or both.

SUMMARY

An object of the present invention is a method, apparatus and program product for image reconstruction of the described type with improved aliasing and noise handling.

This object is achieved in accordance with the attached claims.

Briefly, the present invention reconstructs an image from the derivative of a sinogram by multiplying a projection orientation unit vector field with the derivative to form an oriented derivative, back-projecting the oriented derivative and Riesz transforming the back-projected oriented derivative.

BRIEF DESCRIPTION OF THE DRAWINGS

The invention, together with further objects and advantages thereof, may best be understood by making reference to the following description taken together with the accompanying drawings, in which.

DETAILED DESCRIPTION

Figure 1:
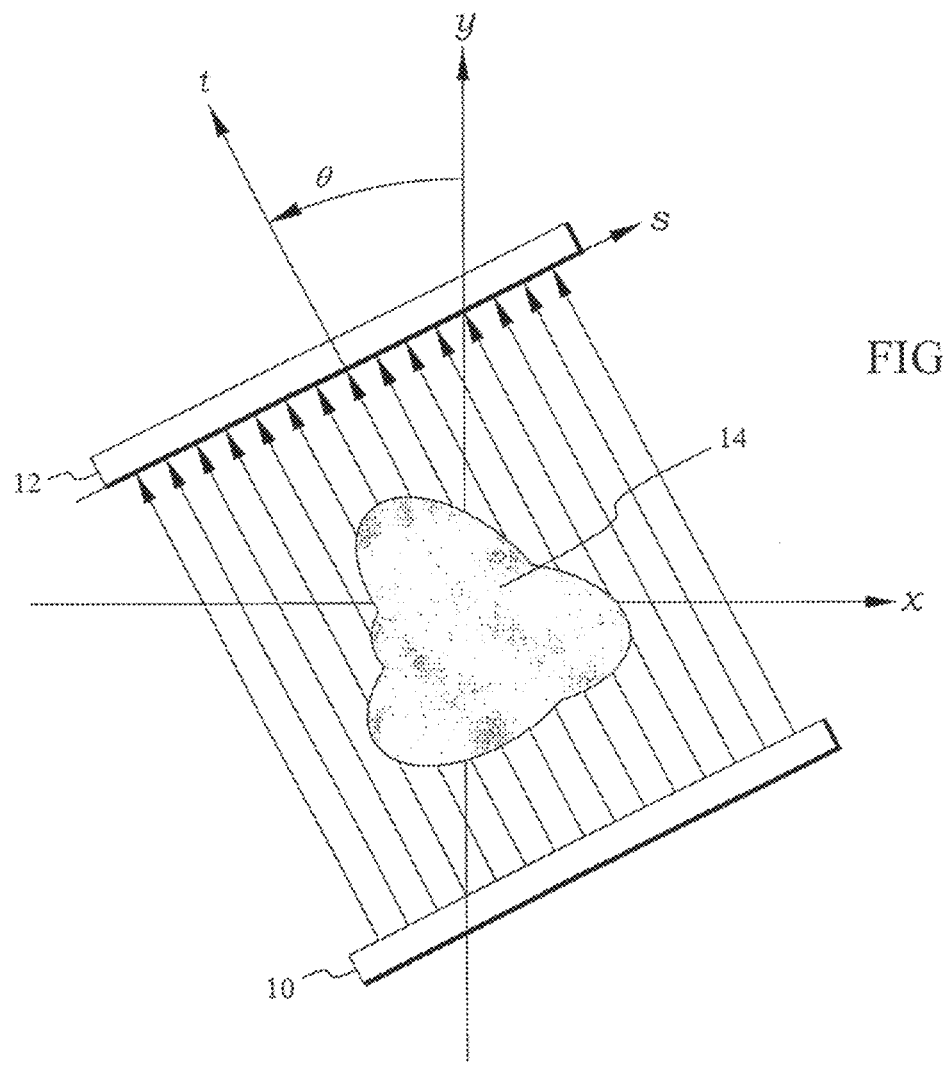
FIG. 1 illustrates a typical arrangement for obtaining line projections.
Figure 2:
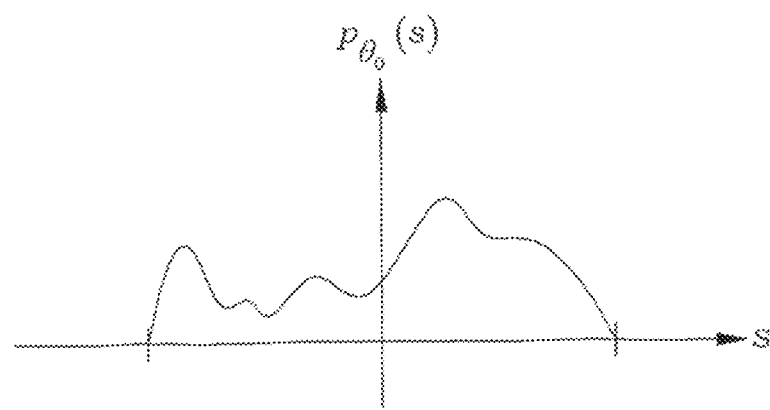
FIG. 2 is a diagram illustrating example line projections.

FIG. 1 illustrates a typical arrangement for obtaining line projections. Neglecting a number of physical side-effects, the image reconstruction problem can be simplified to the following 2D setting. The measuring unit is idealized to include a source 10 emitting parallel rays, for example x-rays, and a detector 12 measuring the intensity of each incoming ray. An object 14 between source 10 and detector 12 attenuates the rays depending on its density. Hence, the total attenuation measured at the detector 12 is the cumulated attenuation of the line through the object 14, i.e., the line projection of the attenuation. The detector 12 includes a number of detector elements, each of which measures a different set of parallel rays, and thus a different line projection for each position s. The whole measuring unit rotates around the object and generates a set of line projections, one for each rotation angle $\theta$. FIG. 2 is a diagram illustrating example line projections $p_{\theta_0}(s)$ for a given rotation angle $\theta_0$.

Figure 3:
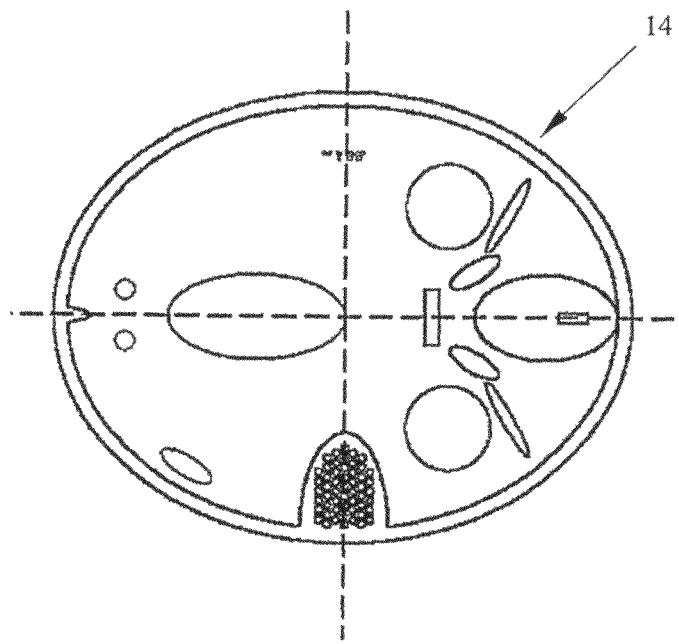
FIG. 3 is a phantom object used to illustrate the present invention.
Figure 4:
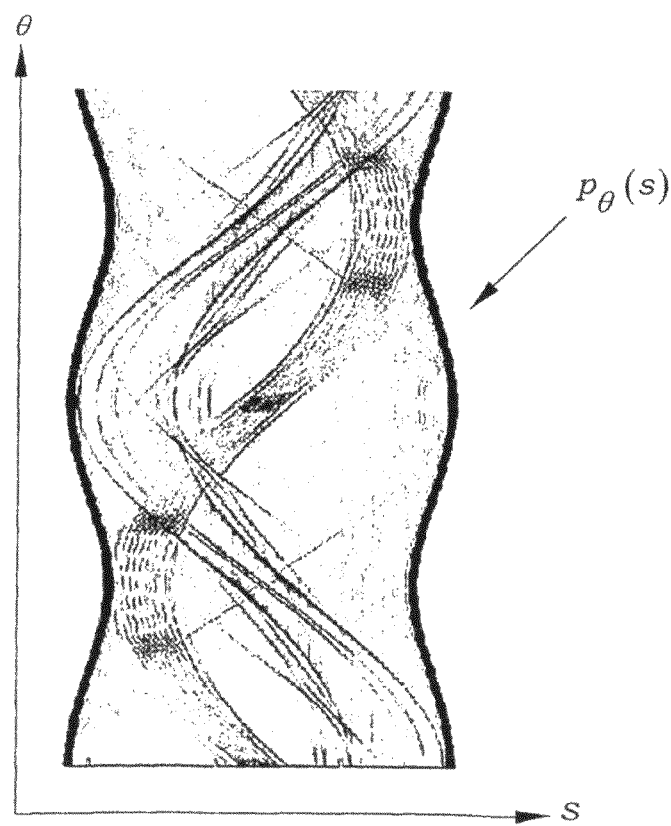
FIG. 4 is a sinogram formed by line projections of the object in FIG. 3.

FIG. 3 is a phantom object 14 (for example a cross-section or slice of a three-dimensional object) that will be used to illustrate the present invention. By determining line projections $p_\theta(s)$ of this object for each angle $\theta$ between 0 and 360 degrees (or between 0 and 180 degrees), one obtains the diagram illustrated in FIG. 4. This diagram is called a sinogram and represents the measured intensities for all detectors (s) and all orientations ($\theta$). Although the term sinogram is most often used for medical applications, for the purposes of the present invention it will be used for both medical and non-medical applications.

The problem to be solved in order to reconstruct the image is to determine the 2D density distribution of the object (slice) from the set of its line projections, i.e. from the sinogram.

In order to describe the image reconstruction problem in mathematical terms, some symbols have to be defined. The object 14 is located at the origin of the 2D coordinate system $(x,y)^T$, where T denotes the transpose. The coordinate system of the detector 12 is denoted $(s,t)^T$ and is rotated by $\theta$ around the origin. The relationship between the two coordinate systems is thus given by:

$$\begin{pmatrix} s \\ t \end{pmatrix} = \begin{pmatrix} \cos\theta & \sin\theta \\ -\sin\theta & \cos\theta \end{pmatrix} \begin{pmatrix} x \\ y \end{pmatrix} = R(\theta)\begin{pmatrix} x \\ y \end{pmatrix} \quad (1)$$

Note that the s-axis was moved to the detector 12 in FIG. 1 in order to visualize that s also represents the position on the detector.

If the density f(x,y) of the object were known, the line projections $p_\theta(s)$ could be obtained mathematically by integrating the density f(x,y) of object 14 along t, i.e.:

$$P_\theta(s) = \int_{-\infty}^{\infty} f(x,y)dt = \int_{-\infty}^{\infty} f(s\cos\theta - t\sin\theta, s\sin\theta + t\cos\theta)dt \quad (2)$$

This linear operator is named the Radon transform after its inventor, see [1]. From linear operator theory it is known that the Radon transform can be inverted by a linear operator and Radon himself suggested one method in [1]. Thus, by measuring $p_\theta(s)$ (the sinogram) one could in principle reconstruct the density $f(x,y)$ (the image).

As shown in APPENDIX I a general expression for reconstructing $f(x,y)$ from the line projections $p_\theta(s)$ is given by:

$$f(x, y) = \int_0^\pi \int_{-\infty}^\infty p_\theta(s) \left( \int_{-\infty}^\infty \exp(i2\pi m(x\cos\theta + y\sin\theta - s))|m|dm \right) ds d\theta \quad (3)$$

The 1D inverse Fourier transform $$\int_{-\infty}^\infty \exp(i2\pi m(x\cos\theta + y\sin\theta - s))|m|dm \quad (4)$$

included in (3) could in principle be integrated out (the expression (4) may be considered as an 1D inverse Fourier transform, since ($x \cos \theta + y \sin \theta - s$) may be considered as a variable that is independent of m), but the presence of the functional determinant |m| leads to convergence problems. Various methods for solving these problems have been suggested in the literature. The most relevant of these prior art methods have been summarized in FIG. 5.

Figure 5:
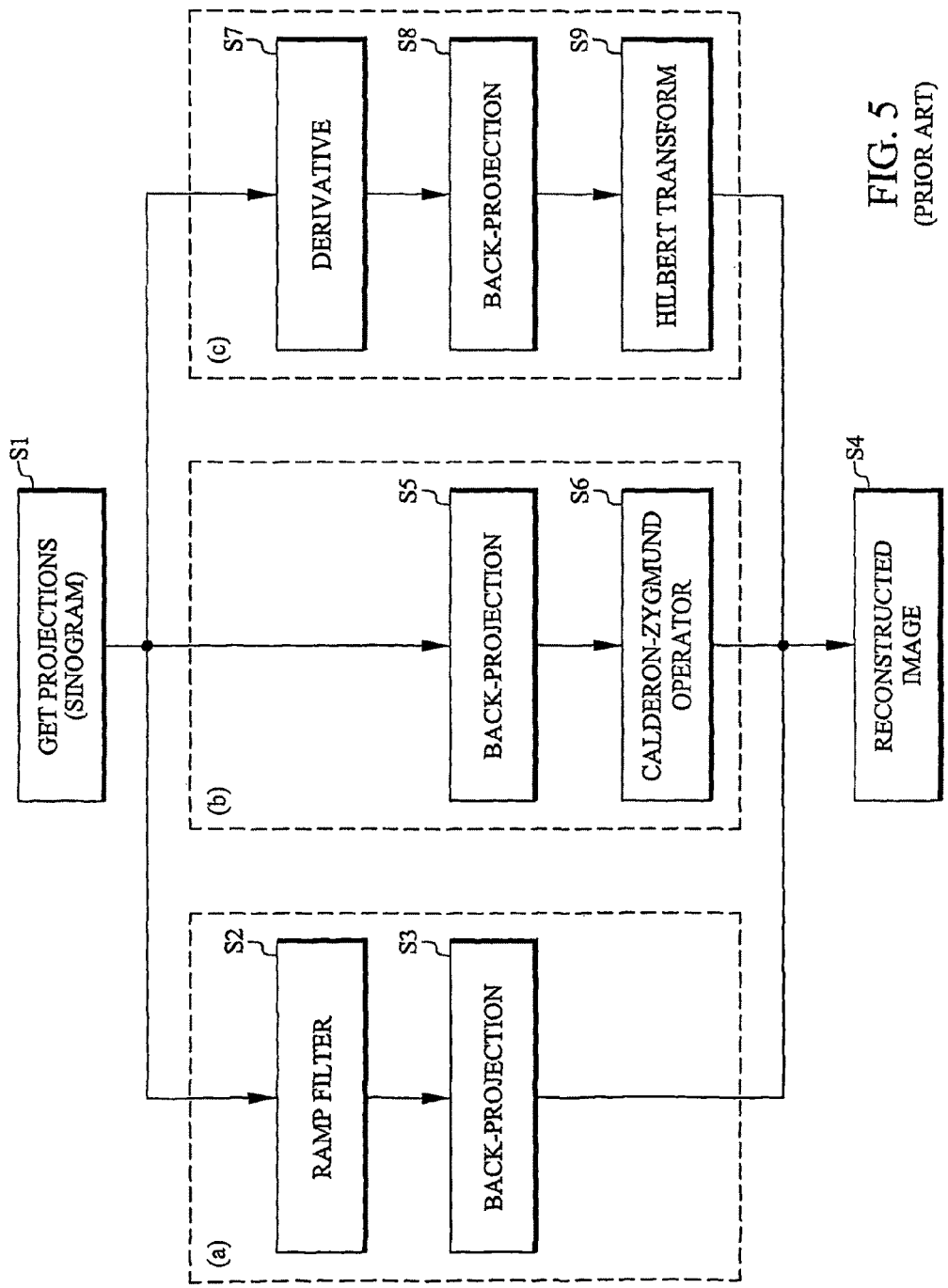
FIG. 5 is a flow chart illustrating prior art image reconstruction methods.

In FIG. 5 the various reconstruction methods start in step S1 by determining the line projections that form the sinogram. The most common way to solve the convergence issue is to pre-filter the sinogram $p_\theta(s)$ with a 1D ramp filter corresponding to |m|, as illustrated in FIG. 5(a). Denoting the ramp-filtered projection as $p_\theta^r(s)$ gives $$f(x, y) = \int_0^\pi \int_{-\infty}^\infty p_\theta^r(s) \left( \int_{-\infty}^\infty \exp(i2\pi m(x\cos\theta + y\sin\theta - s))dm \right) ds d\theta \quad (5)$$

$$= \int_0^\pi \int_{-\infty}^\infty p_\theta^r(s) \delta(x\cos\theta + y\sin\theta - s) ds d\theta$$

$$= \int_0^\pi p_\theta^r(x\cos\theta + y\sin\theta) d\theta$$

The last integral is called a back-projection. More generally an integral having the form $$\int_0^\pi a(\theta)b(x\cos\theta + y\sin\theta) d\theta \quad (6)$$

where $a(\theta)$ is a general (possibly complex or vector valued) function of $\theta$ and b is a function of $s=x \cos \theta+y \sin \theta$, will be denoted a back-projection.

In the method of FIG. 5(a) the back-projection is performed in step S3. The back-projection results in the reconstructed image, as indicated by S4.

Another prior art reconstruction method illustrated in FIG. 5(b) is based on the Calderon-Zygmund operator. Due to symmetry reasons in the Fourier kernel, one can move the factor |m| in (3) to a corresponding factor $\sqrt{u^2+v^2}$ in the 2D domain, resulting in the Calderon-Zygmund operator. This operator establishes a linear post-filtering step S6 after the back-projection S5, in accordance with:

$$f(x, y) = \left[ \int_{-\infty}^\infty \sqrt{u^2 + v^2} \exp(i2\pi(ux + vy)) du dv \right] * \left[ \int_0^\pi p_\theta(x\cos\theta + y\sin\theta) d\theta \right] \quad (7)$$

In (7) the back-projection is represented by the rightmost parenthesis and the notation "*" denotes convolution.

A third prior art reconstruction method illustrated in FIG. 5(c) and described in [2] is based on the Hilbert transform kernel. According to this method the factor |m| is split into two factors $$|m| = (-i\,\text{sign}(m))(im) = \left(-i\frac{m}{|m|}\right)(im) \quad (8)$$

where i is the imaginary unit. The first factor is the Fourier transform of the Hilbert transform kernel and the second factor corresponds to the derivative in the spatial domain (up to a factor $2\pi$). The first factor is computed in the 2D domain, resulting in $-i\text{sign}(v)$ (as v does not undergo a sign-change on the integration interval $(0, \pi)$). This gives $$f(x, y) = 2\pi h(y) * \left[ \int_0^\pi p'_\theta(x\cos\theta + y\sin\theta) d\theta \right] \quad (9)$$

where $$h(y) = \frac{1}{\pi y}$$

denotes the kernel of the vertical Hilbert transform (in the y-direction) and $$p'_\theta(x\cos\theta + y\sin\theta) = \frac{d p_\theta(s)}{ds}\bigg|_{s=x\cos\theta+y\sin\theta} \quad (10)$$

denotes the derivative of the projection. In this case the reconstruction is performed in three steps: first the derivative $p'_\theta$ is formed in step S7, then this derivative is back-projected in step S8 and finally the back-projection is convolved with the Hilbert transform kernel $h(y)$ in step S9. The convolution in (9) is one way to compute the Hilbert transform. $\mathcal{H}_y\{.\}$ (in the y-direction) of the back-projection, i.e.

$$f(x, y) = 2\pi \mathcal{H}_y \left\{ \int_0^\pi p'_\theta(x\cos\theta + y\sin\theta) d\theta \right\} \quad (11)$$

A variation of the Hilbert transform method is described in [3]. According to this method $f(x,y)$ is obtained as $$f(x, y) = 2\pi \mathcal{H}_r \left\{ \begin{array}{l} \frac{\partial}{\partial x}\left(\int_0^\pi p_\theta(x\cos\theta + y\sin\theta)\cos\theta d\theta\right) + \\ \frac{\partial}{\partial y}\left(\int_0^\pi p_\theta(x\cos\theta + y\sin\theta)\sin\theta d\theta\right) \end{array} \right\} \quad (12)$$

(The author of [3] uses a different parameterization and ignores the pre-factor $2\pi$, which is only a scaling factor.)

In accordance with the present invention the Calderon-Zygmund operator given in (7) is split into two vector parts forming a scalar product $$\sqrt{u^2+v^2} = \left\langle -i\frac{(u,v)^T}{\sqrt{u^2+v^2}} \middle| i(u,v)^T \right\rangle = \langle R(u,v) | i(u,v)^T \rangle \quad (13)$$

where $\langle .|. \rangle$ denotes the scalar product and $(.,.)^T$ denotes the transpose. The left vector $R(u,v)$ corresponds to the Fourier transform of the Riesz transform kernel (also denoted the Fourier multiplier of the Riesz transform) described in [4] and the right vector $i(u,v)^T$ corresponds to the 2D gradient in the spatial domain (up to a factor of $2\pi$). According to [5] the 2D gradient may be written as $$\begin{pmatrix} \cos\theta \\ \sin\theta \end{pmatrix} p'_\theta(s) \quad (14)$$

in the projection domain. This leads to the reconstruction formula $$f(x,y) = 2\pi r(x,y) \cdot \left[ \int_0^\pi \begin{pmatrix} \cos\theta \\ \sin\theta \end{pmatrix} p'_\theta(x\cos\theta + y\sin\theta)\, d\theta \right] \quad (15)$$

where $r(x,y)$ denotes the 2D Riesz transform kernel $$r(x,y) = \frac{1}{2\pi}\frac{(x,y)^T}{(x^2+y^2)^{3/2}} \quad (16)$$

The convolution operator "●" in the reconstruction (15) should be interpreted similar to a scalar product, i.e., the first and second component of $r(x,y)$ should be convolved with the first and second component, respectively, of the integral. The convolution in (15) is one way to compute the Riesz transform $\mathcal{R}\{.\}$ of the back-projection, i.e.

$$f(x,y) = 2\pi\mathcal{R}\left\{ \int_0^\pi \begin{pmatrix} \cos\theta \\ \sin\theta \end{pmatrix} p'_\theta(x\cos\theta + y\sin\theta)\, d\theta \right\}. \quad (17)$$

It is noted that in this case both the back-projection and Riesz transform operator are vector-valued.

Figure 6:
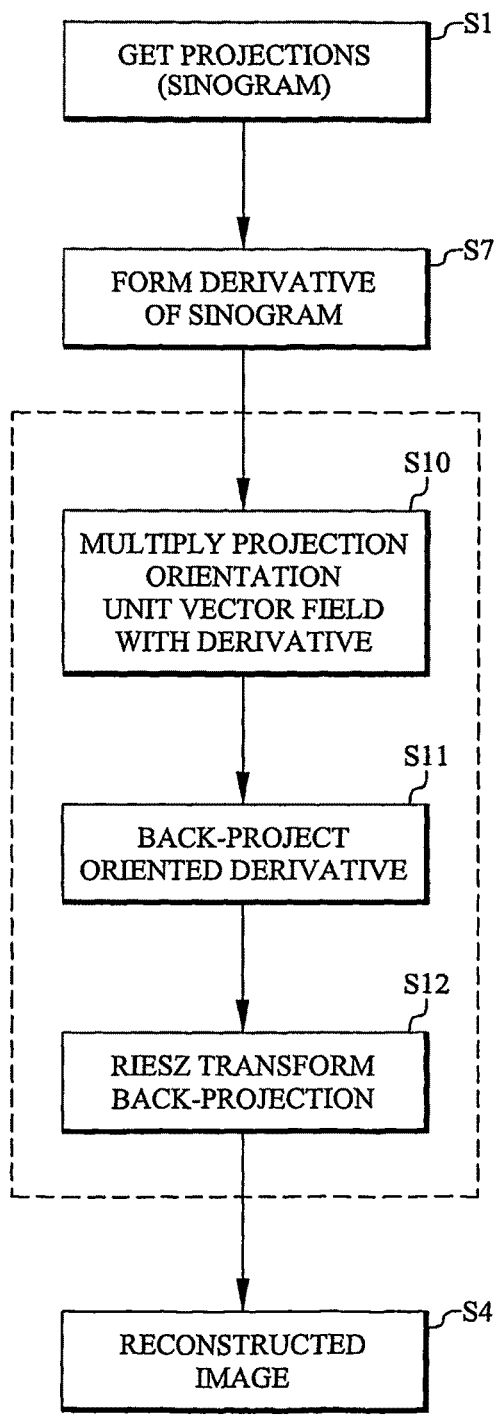
FIG. 6 is a flow chart illustrating an embodiment of the image reconstruction method in accordance with the present invention.

FIG. 6 is a flow chart illustrating the image reconstruction method in accordance with the present invention. Steps S1 and S7 are the same as in FIG. 5(c). Step S10 multiplies the projection orientation unit vector field $(\cos\theta, \sin\theta)^T$ with the derivative of the sinogram to form an oriented derivative. Step S11 back-projects the oriented derivative by integrating it over all orientations $\theta$. Finally step S12 completes the reconstruction by taking the Riesz transform of the back-projection.

Figure 7:
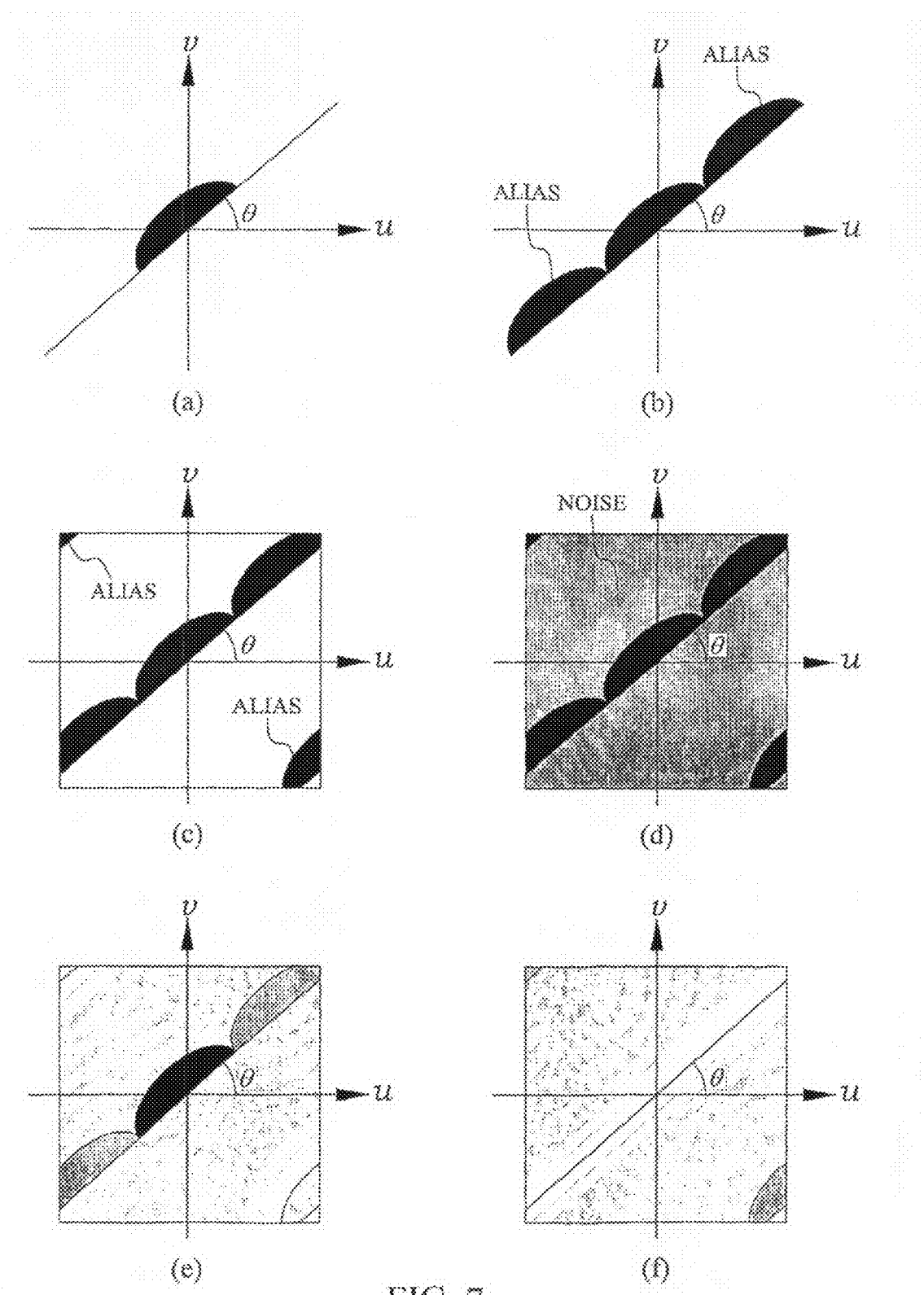
FIG. 7 is a series of diagrams illustrating the effects of aliasing in the Fourier domain.

The advantages of the 2D two-step method in accordance with the present invention compared to the filter back-projection and the two-step Hilbert method become more apparent by considering discrete signals. Assume an arbitrary, but fixed ratio of resolutions on the detector (projection domain) and in the reconstructed image. In the back-projection we will always find orientations such that the back-projected signal suffers from aliasing, see FIG. 7. FIG. 7(a) illustrates the ideal case with a continuous signal and a continuous projection at orientation $\theta$, i.e. there is no aliasing. FIG. 7(b) illustrates aliasing due to periodic repetition of the spectrum of the discrete projection data on the slice at orientation $\theta$. FIG. 7(c) illustrates aliasing due to periodic repetition of the image, leading to projection data not lying on the slice at orientation $\theta$. In addition to aliasing, non-oriented noise will typically cover all angles in the spectrum, as illustrated by the dark gray layer in FIG. 7(d).

The aliasing components have an unsuitable orientation in the image. Applying the one-step reconstruction methods (5), (7) leads to aliasing artifacts in the reconstruction. This is somewhat improved by (9), as the symmetric alias components compensate each other under the Hilbert transform. However, the Hilbert transform, due to its 1D nature, maintains noise components that do not lie on the v-axis. The variation of the Hilbert transform method represented by (12) leads to a somewhat lower noise level than the original Hilbert transform method, but re-introduces the aliasing artifacts of the filtered back-projections. The method is based on multiplying the sinogram with the projection orientation vector. Before the Hilbert transform, the divergence of the back-projected vector field is computed. This means, however, that the back-projection is not formed on the derivative, which implies that one of the major advantages of the original Hilbert transform method is lost.

In (15) the Riesz transform, which is a 2D transform, actually projects the back-projected gradients onto the main orientation $\theta$, which leads to a reduction of all alias components with a factor $|\cos(\Delta\theta)|$ and a noise reduction by a factor of two, see FIG. 7(e). A first-order estimate of the alias components and the noise level in the respective back-projections is illustrated in FIG. 7(f) (in FIGS. 7(e) and 7(f) the white regions correspond to regions where $|\cos(\Delta\theta)|$ and $|\sin(\Delta\theta)|$ are approximately zero). It is represented by the curl component or cross-combinations which are omitted in the definition of the convolution operator "●" in the reconstruction (15). In the ideal continuous case this would involve $$\left\langle -i\frac{(v,-u)^T}{\sqrt{u^2+v^2}} \middle| i(u,v)^T \right\rangle = \frac{vu-uv}{\sqrt{u^2+v^2}} = 0 \quad (18)$$

However, in the discrete case the result is non-zero.

An interesting part of the digital implementation in general is the computation of the Riesz transform on a finite domain. The ideal setting would be to restrict the computation to a circular domain, but practical considerations require a rectangular domain. The reasons are twofold: a) images are typically rectangular shaped (visualization argument) and b) the rectangular domain solution can be computed by FFT algorithms (complexity argument). In experiments an implementation similar to the one described in [6] has been used. The main difference is the different boundary conditions that have to be considered.

Assume that the signal which is to be reconstructed has a compact support (the image has a finite size). Consequently, all projections have a finite support and so do the derivatives. Applying the back projection to the projection derivatives, however, results in a 2D function with infinite support. This can easily be verified by either considering the projection geometry or the non-locality of the Riesz kernel. If we simply back-project onto a finite image, we cut off the tails of the filtered gradient image. Hence, our task becomes to compute the Riesz transform of an infinite signal which is truncated. If we apply a DFT (Discrete Fourier Transform) to the image, this may result in an error in the reconstruction as we neglected the existence of these tails. Fortunately, we know that the 2D signal is zero outside the considered domain. This may be exploited by the following trick, which may be used in a preferred embodiment.

Assume that $$b(x, y) = \int_0^\pi \binom{\cos\theta}{\sin\theta} p'_\theta(x\cos\theta + y\sin\theta) d\theta \quad (19)$$

is the back-projected oriented derivative on the domain $(x,y) \in (0;x_{MAX}) \times (0;y_{MAX})$. Define the modified signal $b_m(x,y)$ on the extended domain $(x,y) \in (-x_{MAX};x_{MAX}) \times (-y_{MAX};y_{MAX})$ by $$b_m(x, y) = \begin{cases} b(x, y) & x > 0, y > 0 \\ \overline{b}(-x, y) & x < 0, y > 0 \\ -\overline{b}(x, -y) & x > 0, y < 0 \\ -b(-x, -y) & x < 0, y < 0 \\ 0 & \text{otherwise} \end{cases} \quad (20)$$

where $\overline{b}$ represents the back-projection with the second component of b having a reversed sign. In this way the components of b are mirrored at the coordinate axes, with anti-symmetry with respect to the y- and x-axis, respectively. As a result, the signal tails which typically exist in the gradient-like or oriented image b compensate each other to a large extent and a more accurate computation of the Riesz transform with finite data becomes possible.

Figure 8:
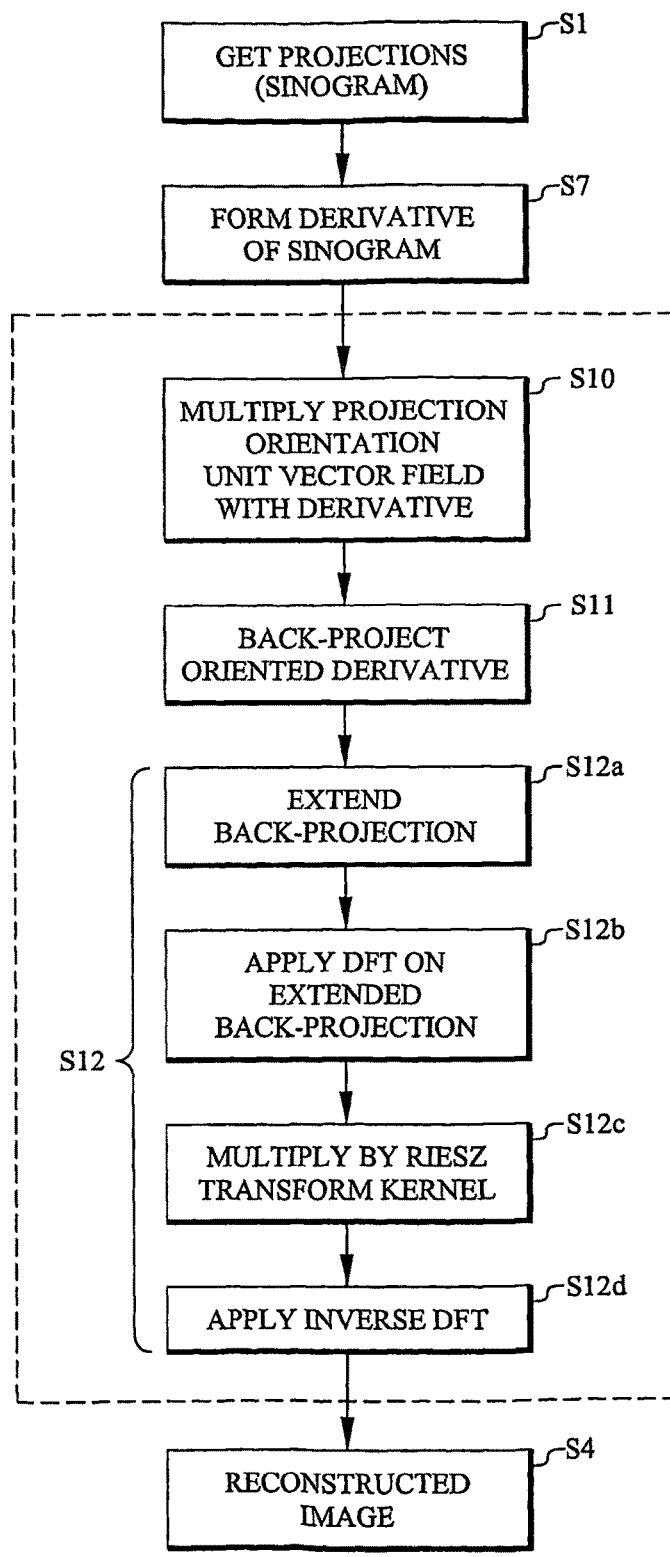
FIG. 8 is a flow chart illustrating another embodiment of the image reconstruction method in accordance with the present invention.

The Riesz transform of the signal $b(x,y)$ under the constraint of zero continuation outside of $(x,y) \in (0;x_{MAX}) \times (0;y_{MAX})$ may now be computed using the DFT and the Fourier multiplier of the Riesz transform:

$$\mathcal{R}\{b\} = IDFT\left(-i\frac{(u, v)^T}{\sqrt{u^2 + v^2}} \middle| DFT(b_m)\right) \quad (21)$$

where IDFT is the inverse DFT. Note that the DFT and IDFT have been applied since all considered signals are discrete in practice. FIG. 8 is a flow chart illustrating this procedure. In FIG. 8 step S12 has been split into steps S12a-S12d. Step S12a extends the back-projection in accordance with (20). Step S12b applies a DFT on the extended back-projection. Step S12c multiplies the DFT by the Riesz transform kernel. Step S12d applies an inverse DFT to the result from step S12c. The reason for the DFT-IDFT steps (S12b and S12d) is that the convolution is more conveniently performed in the frequency domain, where it corresponds to a simple multiplication (step S12c).

In a practical implementation the derivative and the orientation vector field, respectively, are typically represented using complex numbers. In this way, ordinary (scalar) back-projection can be transparently used by simply replacing real interpolation with complex interpolation. If complex numbers are used for embedding 2D vectors, i.e.

$$\langle (u,v)^T | (x,y)^T \rangle = Re\{(u-iv)(x+iy)\} \quad (22)$$

then the sign of the v-component has to be flipped and the projection onto the real part has to be performed after the inverse DFT. Thus, in such an implementation the image is reconstructed as:

$$f(x, y) = Re\left(IDFT\left(-i\frac{u - iv}{\sqrt{u^2 + v^2}} DFT(b_m)\right)\right) \quad (23)$$

APPENDIX II demonstrates a practical implementation of this procedure in MATLAB® code. This embodiment represents the back-projection as complex numbers and uses the fast Fourier transform and inverse fast Fourier transform to implement the DFT and IDFT, respectively.

Figure 9:
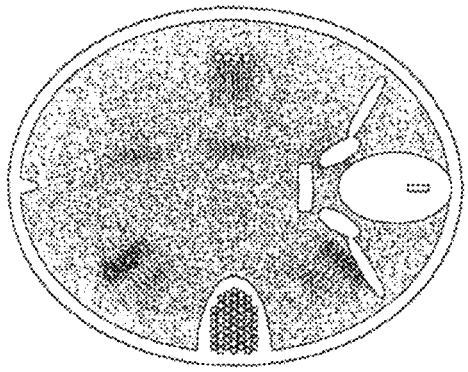
FIG. 9 is a series of images that have been reconstructed in accordance with the prior art and in accordance with the present invention.
Figure 9:
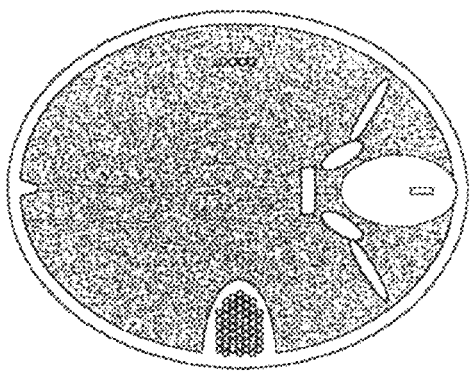
Figure 9:
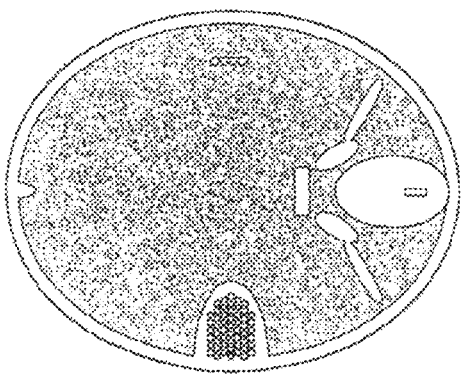
Figure 9:
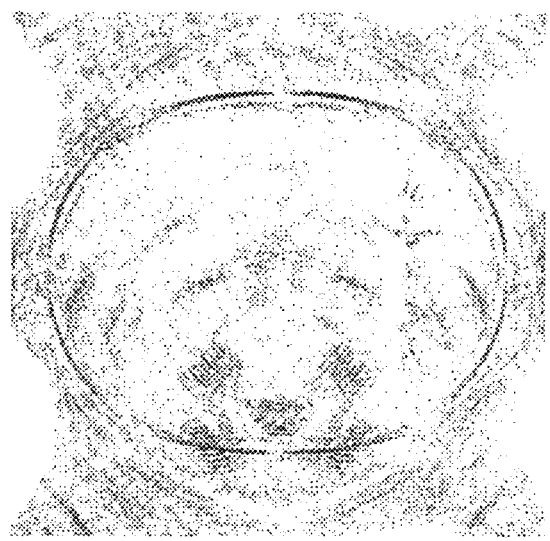

FIG. 9 is a series of images that have been reconstructed in accordance with the prior art and in accordance with the present invention. In all cases the reconstruction is based on the sinogram in FIG. 4, which has been obtained from the object in FIG. 3.

The reconstructed image in FIG. 9(a) has been obtained by the filtered back-projection method in FIG. 5(a). Comparing this to the original image in FIG. 3 illustrates both the resulting noise and aliasing effects.

The reconstructed image in FIG. 9(b) has been obtained by the Hilbert transform method in FIG. 5(c). The two-step Hilbert transform method shows a higher level of noise as the standard deviation of the noise measured along the dashed lines in FIG. 3, right, is more than 10% higher for the Hilbert transform method than for the Riesz transform method in accordance with the present invention. Furthermore, the Hilbert transform method introduces streaking artifacts along the orientation of the Hilbert filter which are difficult to compensate.

The reconstructed image in FIG. 9(c) has been obtained by the Riesz transform method as implemented in APPENDIX II. It is noted that the noise level is lower and that the aliasing has been reduced. FIG. 9(d) shows the curl component corresponding to (18) (or the omitted imaginary part in (23)). From FIG. 9(d) it can be seen that certain aliasing effects from the filtered back-projection method have been moved to the discarded curl component.

In order to visualize the intensity images, the Prewitt edge detector available in GIMP (GNU Image Manipulation Program) has been applied to all reconstructed images. For this reason the streaking artifacts mentioned in connection with the Hilbert transform method are actually not visible as they are of low frequency and thus are suppressed by the Prewitt detector.

In the reconstruction formula (17), each pixel value is reconstructed from an orientation signature resulting from different projections. In the case of truncated projections (for example when the rays in FIG. 1 do not illuminate the entire object at all angles), a part of this signature is missing. Hence, the reconstruction is incomplete. If at least one projection is complete, which is our premise in what follows, we can quantify the missing intensity as $$L(\theta) = \max_{\theta_0} \int_t p_{\theta_0}(t) dt - \int_t p_\theta(t) dt \quad (24)$$

The aim in what follows is to compensate for the missing intensity without introducing artifacts in the reconstruction. The reconstruction is directly related to harmonic function theory, as the reconstructed image and its Riesz transform are harmonic conjugates. If we want to add intensity without introducing singularities, the added back-projected data (before the Riesz transform) must be the response of a conjugated Poisson kernel. The latter is the Riesz transform of a 2D Poisson kernel, i.e., the final reconstruction is complemented or supplemented by the response of a Poisson kernel. However, the scale of the filter is unknown and varies spatially.

Exploiting the fact that line integrals of 2D (conjugates) Poisson kernels yield the corresponding 1D kernels, see [6], we can equally add responses of 1D Poisson kernels to the projection data. The advantage of complementing in the projection domain is twofold: First, the Poisson filter responses do not interfere between different orientations, i.e., we can compute them separately for each orientation. Second, the parameters of the response (amplitude and scale) can be estimated from $L(\theta)$ and the respective projection $p_\theta(t)$.

The 1D Poisson filter (or Cauchy kernel) with scale s is given by:

$$h(t, s) = \frac{s}{\pi(t^2 + s^2)} \quad (25)$$

and its integral is 1. Requiring a continuous extension of the projection data, we introduce an amplitude $A(\theta)$ and require that $$A_l(\theta)h(0, s_l(\theta)) = p_\theta(t_l) \text{ and } A_r(\theta)h(0, s_r(\theta)) = p_\theta(t_r) \quad (26)$$

at the left boundary $t_l$ and right boundary $t_r$, respectively, of the projection data.

Since $$h(0, s) = \frac{1}{\pi s},$$

we obtain $$A_l(\theta) = \pi s_l(\theta) p_\theta(t_l) \text{ and } A_r(\theta) = \pi s_r(\theta) p_\theta(t_r) \quad (27)$$

The scale of the Poisson filters is computed from the constraint that the left and right complement add exactly the right amount of intensity $L(\theta)$, i.e.

$$\int_0^\infty A_l(\theta)h(t, s_l(\theta)) + A_r(\theta)h(t, s_r(\theta)) dt = \quad (28)$$

$$A_l(\theta) + A_r(\theta) =$$

$$\pi(s_l(\theta)p_\theta(t_l) + s_r(\theta)p_\theta(t_r)) = L(\theta)$$

Thus we have a single constraint and two unknowns. There are different possible choices to solve the second degree of freedom, e.g., the intensity can be shared equally between left and right extension or it can be shared in proportion to the projection value at the respective boundary. In the latter case the scales are equal, i.e.

$$s_l(\theta) = s_r(\theta) = \frac{L(\theta)}{\pi(p_\theta(t_l) + p_\theta(t_r))} \quad (29)$$

APPENDIX III includes an example of MATLAB® code for performing the compensating procedure described above.

Figure 10:
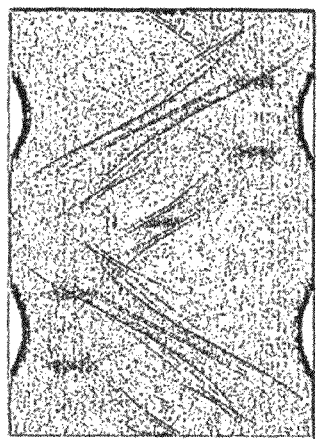
FIG. 10 illustrates a truncated sinogram and its reconstruction.
Figure 10:
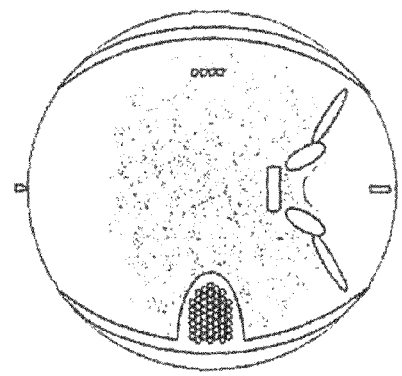
Figure 11:
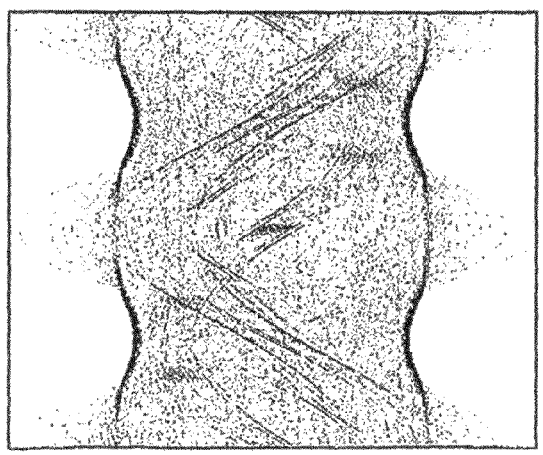
FIG. 11 illustrates a supplemented truncated sinogram and its reconstruction.
Figure 11:
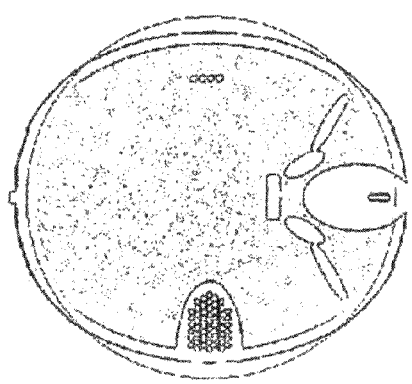

The effects of the compensating procedure are illustrated in FIGS. 10 and 11. FIG. 10 illustrates a truncated sinogram and its reconstruction without compensation for truncations. FIG. 11 illustrates a truncated sinogram and its reconstruction, but in this case truncations in the projection domain are compensated for by adding Poisson tails before computing the derivative. Equal scales have been used. The resulting reconstruction is correct within the region of interest, i.e., the circle which is completely projected. Outside the region of interest, no attempt is made to extrapolate.

Figure 12:
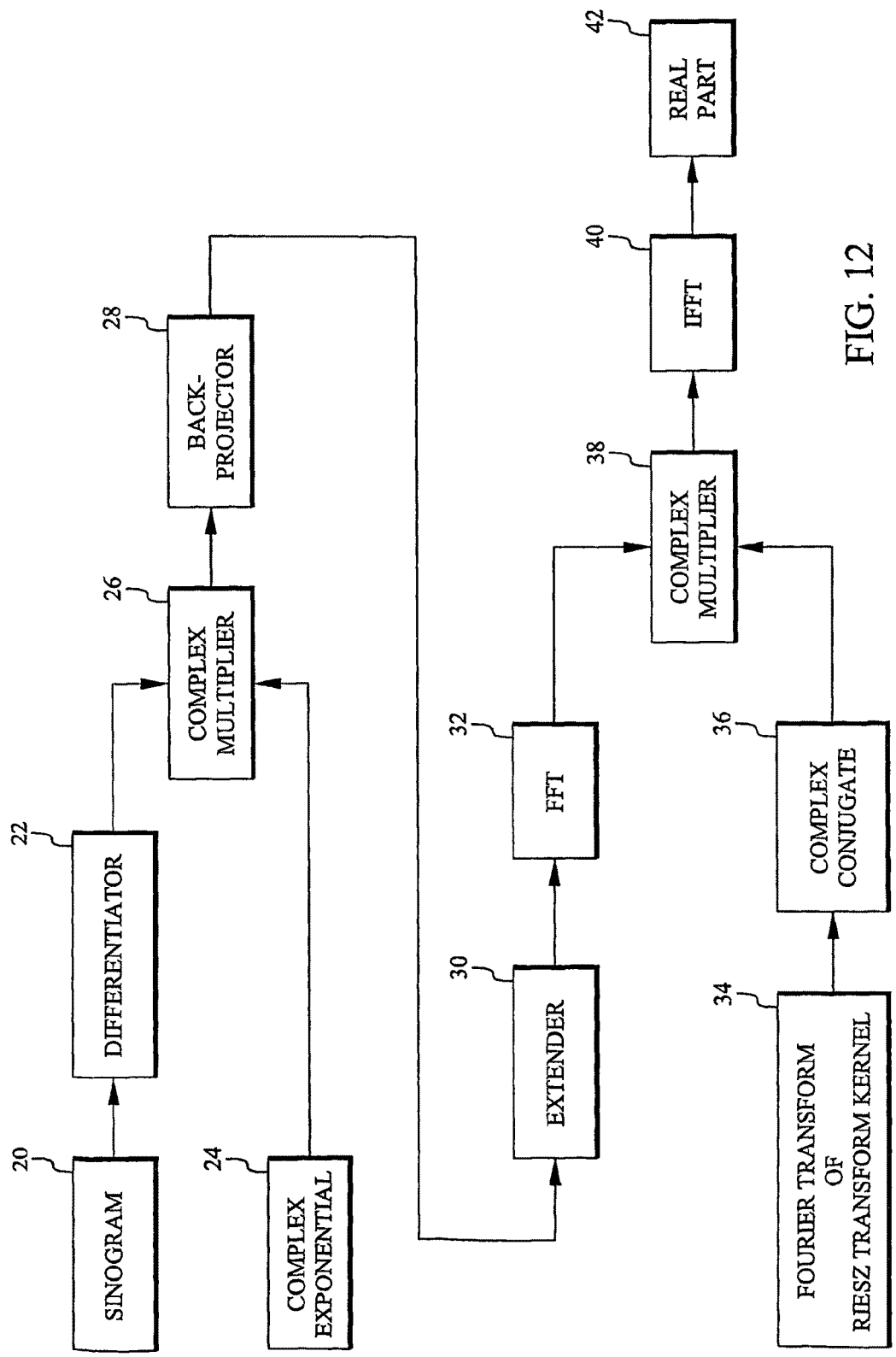
FIG. 12 is a block diagram of an embodiment of an image reconstruction apparatus in accordance with the present invention.

FIG. 12 is a block diagram of an embodiment of an image reconstruction apparatus in accordance with the present invention. This embodiment is based on the complex number representation described in APPENDIX II. A sinogram is retrieved from a storage unit 20 and forwarded to a differentiator 22. The projection orientation unit vector field is obtained as the corresponding complex vectors of the complex exponential function, which are stored in a storage unit 24. The derivatives from differentiator 22 multiply or scale the complex unit vectors in a complex multiplier unit 26. The result is back-projected in a back-projector 28. The back-projection is extended (as described with reference to (20)) in an extender unit 30. The extended back-projection is Fourier transformed in an FFT unit 32. A storage unit 34 stores the Fourier transform of the Riesz transform kernel. This is complex conjugated in a unit 36. The result is multiplied by the FFT from unit 32 in a complex multiplier unit 38. The output from unit 38 is transformed by an IFFT unit 40. The reconstructed image is obtained by a unit 42 extracting the real part of the output from IFFT unit 40 (the actual image is obtained by clipping to remove the parts corresponding to the extensions).

Figure 13:
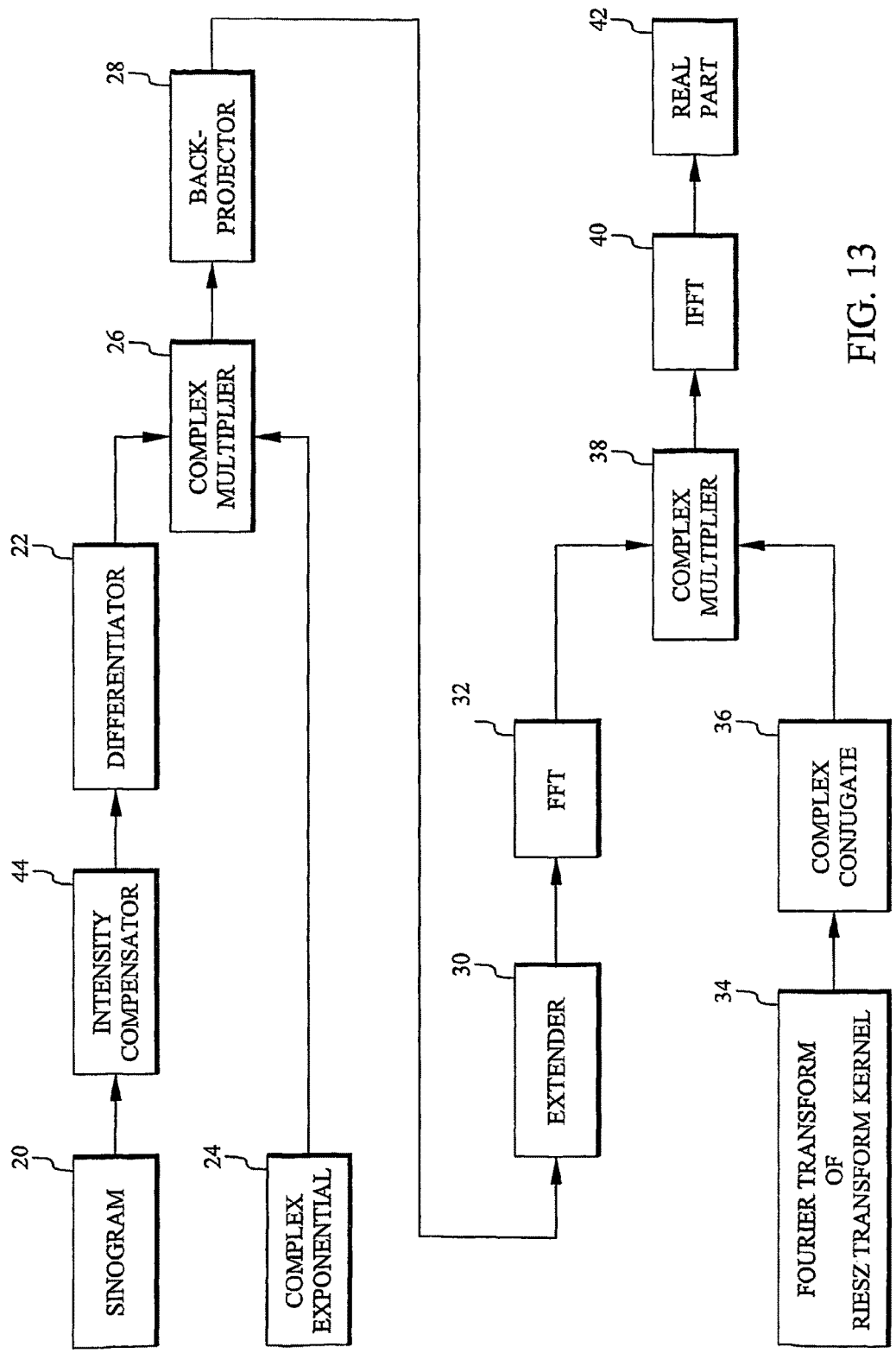
FIG. 13 is a block diagram of another embodiment of an image reconstruction apparatus in accordance with the present invention.

FIG. 13 is a block diagram of another embodiment of an image reconstruction apparatus in accordance with the present invention. This embodiment is essentially the same as the embodiment in FIG. 12, except for the addition of an intensity compensator 44 between sinogram storage unit 20 and differentiator 22. Intensity compensator 44 operates in accordance with the principles describe with reference to APPENDIX III.

In the embodiments of FIGS. 12 and 13 elements 34 and 36 were illustrated as separate elements. However, since the Fourier transform of the Riesz transform kernel is typically stored as a table, these elements could also be combined by storing the complex conjugate of the Fourier transform of the Riesz transform kernel instead.

The image reconstruction apparatus in accordance with the present invention is typically implemented with a micro processor or a micro/signal processor combination and corresponding software. Another possibility is to use an ASIC (Application Specific Integrated Circuit).

It will be understood by those skilled in the art that various modifications and changes may be made to the present invention without departure from the scope thereof, which is defined by the appended claims.

APPENDIX I

The starting point for understanding linear reconstruction techniques is the Fourier slice theorem. In image processing, the 2D Fourier transform of f(x,y) is commonly defined as $$F(u, v) = \int_{-\infty}^{\infty}\int_{-\infty}^{\infty} f(x, y)\exp(-i2\pi(ux + vy))dxdy \quad (30)$$

By elementary calculus one can show that the Fourier transform is invariant under rotations $$F(m, n) = \int_{-\infty}^{\infty}\int_{-\infty}^{\infty} f(s, t)\exp(-i2\pi(ms + nt))ds\,dt \quad (31)$$

where $(m,n)^T = R(\theta)(u,v)^T$ and $R(\theta)$ is defined in (1). Computing the 1D Fourier transform of $p_\theta(s)$ defined in (2) results in $$P_\theta(m) = \int_{-\infty}^{\infty} p_\theta(s)\exp(-i2\pi ms)ds \quad (32)$$

i.e., $P_\theta(m) = F(m,0)$, which results in the Fourier slice theorem. The 2D spectrum F in polar coordinates is obtained as:

$$F(u,v)|_{(u,v)^T = m(\cos\theta,\,\sin\theta)^T} = P_\theta(m) \quad (33)$$

and hence, the original density f(x,y) can be recovered by the inverse Fourier transform as $$f(x, y) = \int_{-\infty}^{\infty}\int_{-\infty}^{\infty} F(u, v)\exp(i2\pi(ux + vy))du\,dv \quad (34)$$

$$= \int_{-\infty}^{\infty}\int_{0}^{\pi} P_\theta(m)\exp(i2\pi m(\cos\theta x + \sin\theta y))|m|d\theta\,dm$$

By inserting the expression for $P_\theta(m)$ in (32), one obtains the reconstruction formula:

$$f(x, y) = \quad (35)$$
$$\int_{0}^{\pi}\int_{-\infty}^{\infty} p_\theta(s)\left(\int_{-\infty}^{\infty} \exp(i2\pi m(x\cos\theta + y\sin\theta - s))|m|\,dm\right)ds\,d\theta$$

APPENDIX II

In this appendix, some MATLAB® code fragments are given to illustrate how the method in accordance with the present invention can be implemented. It is assumed that sinogram contains the projection data. The script starts by calling a helper function dbp( ) which computes the differentiated back-projection. The size of the output image "bild" is fixed to 1024×1024 pixels in this example. The remaining lines are documented inline.
bildrc=dbp(sinogram,1024);
rb4=[bildrc conj(fliplr(bildrc)); -conj(flipud(bildrc)) . . .
flipud(fliplr(bildrc))]; % build symmetric extension of image
RI=fftshift(fft2(rb4)); % switch to Fourier domain
[su,sv]=size(RI); % compute Riesz transform in Fourier
  % domain (start)
[u,v]=meshgrid(-su/2:su/2-1,-sv/2:sv/2-1);
w=-i*(u-i*v);
RRI=w./(eps+abs(w)).*RI; % compute Riesz transform (end)
rri=ifft2(ifftshift(RRI)); % switch to image domain
bild=real(rri(1:1024,1:1024)); % clip relevant (real) part The helper function dbp( ) computes the t-derivatives of the projections and multiplies them with a complex orientation representation. Finally, the result is back-projected into the image domain without further filtering.
function [bildr]=dbp(R,sz)
[sr,st]=size(R);
% differentiation and multiplication with orientation representation:
Rr=diff(R).*(ones(sr-1,1)*exp(-i*(0:st-1)/st*2*pi));
th=(0:st-1)./st.*360;
bildr=iradon(Rr,th,'none',sz); % back-projection without pre-filter

APPENDIX III

In case of truncated projections, the suggested method for extending the projections before back-projection can be applied. The code-fragment below could serve as an example for doing this before calling the main script in APPENDIX II.
% compute L(theta)
L=max(0,max(sum(sinogram))-2-sum(sinogram));
L(L>0)=1.05*(L(L>0)+2);
% compute A1=A__1 and Aend=A_r
A1=abs(sinogram(1,:));
Aend=abs(sinogram(end,:));
% compute decay factors s1=s__1 and s2=s_r
L1=A1./(A1+Aend+eps).*L;
Lend=Aend./(A1+Aend+eps).*L;
s1=2/pi*L1./A1;
send=2/pi*Lend./Aend;
% create coordinate vectors
x1=ceil(10*max(s1)):-1:1;
xend=1:ceil(10*max(send));
x1=x1';
xend=xend';
% compute filter responses ('tails')
sinotl1=2/pi*(ones(size(x1))*L1).*(ones(size(x1))*s1)./ . . .
(x1.^2*ones(size(L1))+ones(size(x1))*s1.^2);
sinotlend=2/pi*(ones(size(xend))*Lend).*(ones(size(xend))*send)./ . . .
(xend.^2*ones(size(Lend))+ones(size(xend))*send.^2);
% combine final extended sinogram
sinogram=[sinotl1; sinogram; sinotlend];

REFERENCES

[1] J. Radon. On the determination of functions from their integral values along certain manifolds. *IEEE Transactions on Medical Imaging*, 5(4):170-176, December 1986. Translation of the original German text by P. C. Parks.
[2] F. Noo, R. Clackdoyle, and J. D. Pack. A two-step Hilbert transform method for 2d image reconstruction. *Physics in Medicine and Biology*, 49:3903-3923, 2004.
[3] G. L. Zeng. Image reconstruction via the finite Hilbert transform of the derivative of the backprojection. Med. Phys. 34(7), July 2007, pp 2837-2843.
[4] E. M. Stein and G. Weiss. *Introduction to Fourier Analysis on Euclidean Spaces*. Princeton University Press, New Jersey, 1971, pp 221-224.
[5] M. Felsberg and G. Sommer. The monogenic signal. *IEEE Transactions on Signal Processing*, 49(12):3136-3144, December 2001.
[6] M. Felsberg, R. Duits, and L. Florack. The monogenic scale space on a rectangular domain and its features. *International Journal of Computer Vision*, 64(2-3), 2005.

The invention claimed is:
1. A method of reconstructing an image from a derivative of a sinogram ($p_\theta(s)$), comprising:
   multiplying a projection orientation unit vector field with the derivative to form an oriented derivative;
   back-projecting the oriented derivative; and
   Riesz transforming the back-projected oriented derivative.
2. The method of claim 1, further comprising: reconstructing a discrete image with predetermined spatial resolution from the derivative of a discrete sinogram with predetermined spatial and angular resolutions.

3. The method of claim 2, further comprising: extending the back-projected oriented derivative before performing the Riesz transformation.

4. The method of claim 2 or 3, further comprising: performing the Riesz transformation as a convolution.

5. The method of claim 4, further comprising:
applying the discrete Fourier transform to the back-projected oriented derivative;
multiplying the Fourier transformed back-projected oriented derivative by the Fourier transform of the Riesz transform kernel; and
applying the inverse discrete Fourier transform to the product.

6. The method of claim 1, further comprising:
compensating for truncations in the sinogram by adding Poisson tails before computing the derivative of the sinogram.

7. An apparatus for reconstructing an image from a derivative of a sinogram ($p_\theta(s)$), comprising:
means for multiplying a projection orientation unit vector field with the derivative to form an oriented derivative;
means for back-projecting the oriented derivative; and
means for Riesz transforming the back-projected oriented derivative.

8. The apparatus of claim 7, further comprising: means for extending the back-projected oriented derivative before performing the Riesz transformation.

9. The apparatus of claim 8, further comprising: means for performing the Riesz transformation as a convolution.

10. The apparatus of claim 9, further comprising:
means for applying the discrete Fourier transform to the back-projected oriented derivative;
means for multiplying the Fourier transformed back-projected oriented derivative by the Fourier transform of the Riesz transform kernel; and
means for applying the inverse discrete Fourier transform to the product.

11. The apparatus of any of the preceding claims 7-10, further comprising: means for compensating for truncations in the sinogram by adding Poisson tails before computing the derivative of the sinogram.

12. The method of claim 2, further comprising: compensating for truncations in the sinogram by adding Poisson tails before computing the derivative of the sinogram.

13. The method of claim 3, further comprising:
compensating for truncations in the sinogram by adding Poisson tails before computing the derivative of the sinogram.

14. The method of claim 4, further comprising: compensating for truncations in the sinogram by adding Poisson tails before computing the derivative of the sinogram.

15. The method of claim 5, further comprising: compensating for truncations in the sinogram by adding Poisson tails before computing the derivative of the sinogram.

* * * * *